(12) United States Patent
Galley et al.

(10) Patent No.: US 7,858,653 B2
(45) Date of Patent: *Dec. 28, 2010

(54) 2-IMIDAZOLES

(75) Inventors: Guido Galley, Rheinfelden (DE);
Katrin Groebke Zbinden, Liestal (CH);
Roger Norcross, Olsberg (CH); Henri Stalder, Basel (CH)

(73) Assignee: Hoffman-La Roche Inc., Nutley, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/950,446

(22) Filed: Dec. 5, 2007

(65) Prior Publication Data

US 2008/0146634 A1 Jun. 19, 2008

(30) Foreign Application Priority Data

Dec. 13, 2006 (EP) .................. 06126005

(51) Int. Cl.
*A01N 43/50* (2006.01)
*C07D 233/00* (2006.01)

(52) U.S. Cl. .................. 514/398; 548/331.5
(58) Field of Classification Search .............. None
See application file for complete search history.

(56) References Cited

U.S. PATENT DOCUMENTS

| | | | |
|---|---|---|---|
| 2,161,938 A | 6/1939 | Sonn | |
| 2,457,047 A | 12/1948 | Kyrides | |
| 2,731,471 A | 1/1956 | Synerholm et al. | |
| 2,744,909 A | 5/1956 | Speeter | |
| 2,744,910 A | 5/1956 | Speeter | |
| 2,778,836 A | 1/1957 | Morren | |
| 2,919,274 A | 12/1959 | Faust et al. | |
| 3,161,653 A | 12/1964 | Fruhstorfer et al. | |
| 3,354,175 A | 11/1967 | Fruhstorfer et al. | |
| 3,377,247 A | 4/1968 | Elbe | |
| 3,459,763 A * | 8/1969 | Gruenfeld | 548/331.5 |
| 3,586,695 A | 6/1971 | Wysong et al. | |
| 3,622,579 A | 11/1971 | Stahle et al. | |
| 3,660,423 A | 5/1972 | Wysong et al. | |
| 3,758,476 A | 9/1973 | Rippel et al. | |
| 3,818,035 A | 6/1974 | Binon et al. | |
| 3,818,094 A | 6/1974 | Stahle et al. | |
| 3,992,403 A | 11/1976 | Roebke | |
| 4,125,620 A | 11/1978 | Stahle et al. | |
| 4,146,647 A | 3/1979 | Lafon | |
| 4,323,570 A | 4/1982 | Stenzel et al. | |
| 4,665,095 A | 5/1987 | Winn et al. | |
| 5,610,174 A | 3/1997 | Craig et al. | |
| 5,658,938 A | 8/1997 | Geerts et al. | |
| 2002/0019390 A1 | 2/2002 | Wong et al. | |
| 2003/0181354 A1 | 9/2003 | Abdulrazik | |
| 2003/0236274 A1 | 12/2003 | Tasaka et al. | |

FOREIGN PATENT DOCUMENTS

| | | |
|---|---|---|
| CA | 2246027 | 2/2000 |
| DE | 16 95 005 | 2/1971 |
| EP | 0 024 829 | 3/1981 |
| EP | 0 086 043 A1 | 8/1983 |
| EP | 0 125 410 | 11/1984 |
| EP | 0 166 937 | 1/1986 |
| EP | 0 331 374 | 9/1989 |
| EP | 0 424 059 | 4/1991 |
| EP | 0 857 483 | 8/1998 |
| EP | 0 924 209 | 6/1999 |
| EP | 1 103 243 | 5/2001 |
| EP | 1 413 576 | 4/2004 |
| ES | 323 985 | 12/1966 |
| FR | 6 551 | 12/1968 |
| GB | 877306 | 9/1961 |

(Continued)

OTHER PUBLICATIONS

Gruenfeld et al, caplus an 1969:47457.*

(Continued)

*Primary Examiner*—Kamal A Saeed
*Assistant Examiner*—Sun Jae Y Loewe
(74) *Attorney, Agent, or Firm*—George W. Johnston; Patricia S. Rocha-Tramaloni; Gene J. Yao

(57) ABSTRACT

The present invention relates to compounds of formula I,

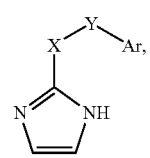

wherein
X is —CH$_2$— or —NH—;
Y is —CH(lower alkoxy)-, —CH(lower alkyl)-, —O—, —S—, —S(O)—, —S(O)$_2$— or —CH$_2$—; and
Ar is phenyl or naphthyl, which rings are optionally substituted by one or two substituents selected from the group consisting of halogen, lower alkoxy, lower alkyl and lower alkyl substituted by halogen;
or a pharmaceutically-acceptable acid-addition salt thereof;
with the proviso that, when X is —NH—, Y is —CH(lower alkyl)- or —CH$_2$—;
and the further proviso that the compound is not
2-phenethyl-1H-imidazole hydrochloride,
2-(3,4-dichloro-phenoxymethyl)-1H-imidazole hydrochloride,
2-(2-chloro-phenoxymethyl)-1H-imidazole hydrochloride,
2-(2,3-dichloro-phenoxymethyl)-1H-imidazole,
benzyl-(1H-imidazol-2-yl)-amine,
(4-chloro-benzyl)-(1H-imidazol-2-yl)-amine, or
(2-chloro-benzyl)-(1H-imidazol-2-yl)-amine.

The invention relates also to a pharmaceutically-acceptable acid-addition salt of such a compound, processes for making the compound, and a composition comprising such a compound.

3 Claims, No Drawings

FOREIGN PATENT DOCUMENTS

| | | |
|---|---|---|
| GB | 1016514 | 1/1966 |
| GR | 1131191 | 10/1968 |
| WO | WO 96/22768 | 8/1996 |
| WO | WO 97/12874 | 4/1997 |
| WO | WO 98/12183 | 3/1998 |
| WO | WO 01/30762 A1 | 5/2001 |
| WO | WO 01/81334 | 11/2001 |
| WO | WO 02/22801 A2 | 3/2002 |
| WO | WO 02/40453 A | 5/2002 |
| WO | WO 02/076950 | 10/2002 |
| WO | WO 03/092374 | 11/2003 |
| WO | WO 2004/014898 | 2/2004 |
| WO | WO 2006/107923 A1 | 10/2006 |
| WO | WO 2006/119411 | 11/2006 |
| WO | WO 2007/024944 | 3/2007 |

OTHER PUBLICATIONS

Freiter, E.R., et al., J. Heterocyclic Chem., vol. 10, No. 3, pp. 391-394 (1973), XP008087527.

Tarnchompoo, B., et al., vol. 31, No. 40, pp. 5779-5780 (1990), XP002118267.

Wilkinson, C.F., et al., Biochem. Pharmacol., vol. 21, pp. 3187-3192 (1972), XP :008087536.

Raddatz, Rita , et al., J. Pharmacol. Exp. Therap., vol. 292, No. 3, pp. 1135-1145 (2000), XP008087488.

Shafiee, A., et al., Journal of Heterocyclic Chemistry, pp. 607-610 (1998), XP001069546.

Robertson, David W., J. Med. Chem., vol. 29, pp. 1577-1586 (1986), XP008087539.

Database CA, Chemical Abstracts, Yamaguchi, Hideaki, XP002465006 & JP 06 268356 (1994).

Altenbach et al., Synthesis and Structure-Activity Studies on N-[5-(1H-Imidazol-4-yl)-5,6,7,8-tetrahydro-1-naphthalenyl]methanesulfonamide, an Imidasole-Containing $\alpha_{1A}$-Adrenoceptor Agonist, J. Med. Chem. (2004), 47: 3220-3235.

Amemiya et al., Synthesis and $\alpha$-Adrenergic Activities of 2-and 4-Substituted Imidazoline and Imidazoline Analogues, J. Med. Chem. (1992), 35:750-755.

Bagley et al., Synthesis and $\alpha_2$-Adrenegeric Activities of Imidazole and Imidazolidine Analogues: In Vitro and In Vivo Selectivity, Medicinal Chemistry Research (1994), 4:346-364.

Branchek et al., Trace amine receptors as targets for novel therapeutics: legend, myth and fact, Curr. Opin. Phamacol. (2003), 3:90-97.

Bunzow et al., Amphetamine, 3,4-Methylenedioxymethamphetamine, Lysergic Acid Diethylamide, and Metabolites of the catecholamine Neurotransmitters Are Agonists of a Rat Trace Amine Receptor, Molecular Pharmacology (2001), 60: 1181-1188.

Carroll et al., In Vitro and In Vivo Characterization of Alpha-1A Selective Agonists and Their Utility For Stress Incontinence, Med. Chem. Res. (2004), 13:134-148.

De Bernardis et al., Conformationally Defined Adrenergic Agents. 3. Modifications to the Carbocyclic Ring of 5,6-Dihydroxy-1-(2-imidazolinyl)tetralin: Improved Separation of $\alpha_1$ and $\alpha_2$ Adrenergic Activities, J. Med. Chem. (1986), 29:1413-1417.

De Bernardis et al., Conformationally Defined Adregernic Agents. 5. Resolution, Absolute Configuration, and Pharmacological Characterization of the Enantiomers of 2-(5,6-Dihydroxy-1,2,3,4-tetrahydro-1-naphthyl)imidazoline: A Potent Agonist at $\alpha$—Adrenoceptors, J. Med. Chem. (1987), 30:1011-1017.

Faust et al., Antihypertensive Agents: Derivatives of 2-Imidazoline and 1,4,5,6-Tetrahydropyrimidine, J. Org. Chem. (1961), 26: 4044-4047.

Hirashima et al., Three-Dimensional Common-Feature Hypotheses for Octopamine Agonist 2-(Arylimino)imidazolidines, Bioorganic & Medicinal Chemistry (2002), 10:117-123.

Holt, A., Imidazoline binding sites on receptors and enzymes:Emerging targets for novel antidepressant drugs?, Journal of Psychiatry & Neuroscience (2003), 28:409-414.

Jetter et al., Synthesis of 4-Substituted Imidazoles via Palladium-Catalyzed Cross-Coupling Reactions, Synthesis (1998), 829-831.

Law et al., Benzylimidazolines as h5-$HT_{1B/1D}$ Serotonin Receptor Ligands: A Structure-Affinity Investigation, J. Med. Chem. (1998), 41:2243-2251.

Lee et al., 4-[(N-Imidazol-2-ylmethyl)aniline]pyranopyridine Analogs as Novel Anti-Angiogenic Agents, Bull. Korean Chem. Soc. (2005), 25: 619-628.

Lindemann et al., A renaissance in trace amines inspired by a novel GPCR family, Trends in Pharmacol. Sci. (2005), 26:274-281.

Lindemann et al., Trace amine-associated receptors form structurally and functionally distinct subfamilies of novel G protein-coupled receptors, Genomics (2005), 85: 372-385.

Matsunaga et al., $C_{17,20}$ inhibitors. Part 2: Design, synthesis and structure-activity relationships of (2-naphthylmethyl)-1H-imidazoles as novel $C_{17,20}$-lyase inhibitors, Bioorganic & Medicinal Chemistry (2004), 4314.

Matsunaga et al., Synthetic studies on (1S)-6,7-dimethoxy-2-naphthyl)-1-(1H-imidazol-4-yl)2-methylpropan-1-ol as a selective $C_{17,20}$-lyase inhibitor, Tetrahedron: Asymmetry (2004), 15: 2021-2028.

McCormack et al., Autoradiographic Localization of Tryptamine Binding Sites in the Rat and Dog Central Nervous System, J. Neurosci. (1986), 6:94-101.

McLennan, P;L., The Hypothermic Effect of Clonidine and Other Imidazolidines in Relation to their Ability to Enter the Central Nervous System in Mice, European Journal of Pharmacology (1981), 69:477-482.

Mosseau et al., A high-affinity [$^3$H]tryptamine binding site in human brain, Prog. Brain Res. (1995), 106:285-291.

Nathanson, J.A.,Phenyliminoimidazolines: Characterization of a Class of Potent Agonists of Octopamine-Sensitive Adenylate Cylcase and Their Use in Understanding the Pharmacology of Octopamine Receptors, Amer. Soc. Pharmacology (1985), 28:254-268.

Ojida et al., Sterocontrolled synthesis of (1S)-1-(1H-imidazol-4-yl)-1-(6-methoxy-2-napthyl)-2-methylpropan-1-ol as a potent $C_{17,20}$-lyase inhibitor,Tetrahedron: Asymmetry (2004), 15: 1555-1559.

Olmos et al., Imidazolines stimulate release of insulin from RIN-5AH cells independently from imidazoline $I_1$ and $I_2$ receptors, European Journal of Pharmacology (1994), 262: 41-48.

Prisinzano et al., 2-(aniline)imidazolines and 2-(benzyl)imidazoline derivatives as h5-$HT_{1D}$ serotonin receptor ligands, Bioorganic & Medicinal Chemistry Letter (2004), 14:4697-4699.

Savola et al., Cardiovascular and Sedative $\alpha$-Adrenoceptor Effects of Detomidine-like Arylalkyl Imidazoles and Associated Derivatives, Drug Res. (1988), 38:29-35.

Timmermans et al., Characterization of $\alpha$-Adrenoceptor Populations. Quantitive Relationships between Cardiovascular Effects Initiated at Central and Peripheral $\alpha$-Adrenoceptors, J. Med. Chem. (1981), 24:502-507.

Timmermans et al., Correlations between Central Hypotensive and Peripheral Hypertensive Effects of Structurally Dissimilar Alpha-Adrenoceptor Agonists, Life Sciences (1981), 28:653-660.

Turner et al., A Facile Route to Imidazol-4-yl Anions and Their Reaction with Carbonyl Compounds, J. Org. Chem. (1991), 56: 5739-5740.

Usdin, E. and M. Sandler, Eds., Psychopharmacology Series, vol. 1: Trace Amines and the Brain (1976), 1-281.

Wentland et al., Syntehsis and Antidepressant Properties of Novel 2-Substituted 4,5-Dihydro-1H-imidazole Derivatives, J. Med. Chem. (1987), 30:1482-1489.

Zhang et al., Medetomidine Analogs as $\alpha_2$-Adrenegeric Ligands. 3. Synthesis and Biological Evaluation of a New Series of Medetomidine Analogs and Their Potential Binding Interactions with $\alpha_2$-Adrenoceptors Involving a "Methyl Pocket", J. Med. Chem. (1997), 40: 3014-3024.

* cited by examiner

2-IMIDAZOLES

PRIORITY TO RELATED APPLICATION(S)

This application claims the benefit of European Patent Application No. 06126005.5, filed Dec. 13, 2006, which is hereby incorporated by reference in its entirety.

FIELD OF THE INVENTION

This invention relates to compounds which have a good affinity to the trace amine associated receptors (TAARs), especially for TAAR1.

These compounds are useful in the treatment or prevention of, inter alia, disorders of the central nervous system, for example, the treatment or prevention of depression, psychosis, Parkinson's disease, anxiety and/or attention deficit hyperactivity disorder (ADHD).

The invention relates also to processes for preparing such compounds and a pharmaceutical composition comprising such a compound.

BACKGROUND OF THE INVENTION

The classical biogenic amines (serotonin, norepinephrine, epinephrine, dopamine, histamine) play important roles as neurotransmitters in the central and peripheral nervous system. Deutch, A. Y. and Roth R. H. (1990) Neurotransmitters. In *Fundamental Neuroscience* (2nd ed.) (Zigmond, M. J., Bloom, F. E., Landis, S. C., Roberts, J. L., and Squire L. R., eds.) 193-234, Academic Press. Their synthesis and storage, as well as their degradation and reuptake after release are tightly regulated. An imbalance in the levels of biogenic amines is known to be responsible for the altered brain function under many pathological conditions. Wong, M. L. and Licinio, J. (2001) *Nat. Rev. Neurosci.* 2, 343-351; Carlsson, A. et al. (2001), *Annu. Rev. Pharmacol. Toxicol.* 41, 237-260; Tuite, P. and Riss, J. (2003), *Expert Opin. Investig. Drugs* 12, 1335-1352; Castellanos, F. X. and Tannock, R. (2002), *Nat. Rev. Neurosci.* 3, 617-628.

A second class of endogenous amine compounds, the so-called trace amines (TAs) significantly overlap with the classical biogenic amines regarding structure, metabolism and subcellular localization. The TAs include p-tyramine, β-phenylethylamine, tryptamine and octopamine, and they are present in the mammalian nervous system at generally lower levels than classical biogenic amines. Usdin, E. and Sandler, M. eds. (1984), *Trace Amines and the brain*, Dekker. Their disregulation has been linked to various psychiatric diseases like schizophrenia and depression and for other conditions like attention deficit hyperactivity disorder, migraine headache, Parkinson's disease, substance abuse and eating disorders. Lindemann, L. and Hoener, M. (2005), *Trends in Pharmacol. Sci.* 26, 274-281; Branchek, T. A. and Blackburn, T. P. (2003), *Curr. Opin. Pharmacol.* 3, 90-97; Premont, R. T. et al. (2001), *Proc. Natl. Acad. Sci. U.S.A.* 98, 9474-9475.

For a long time, TA-specific receptors had only been hypothesized based on anatomically discrete high-affinity TA binding sites in the central nervous system of humans and other mammals. Mousseau, D. D. and Butterworth, R. F. (1995), *Prog. Brain Res.* 106, 285-291; McCormack, J. K. et al. (1986), *J. Neurosci.* 6, 94-101. Accordingly, the pharmacological effects of TAs were believed to be mediated through the well known machinery of classical biogenic amines, by either triggering their release, inhibiting their reuptake or by "crossreacting" with their receptor systems. Premont, R. T. et al. (2001), *Proc. Natl. Acad. Sci. U.S.A.* 98, 9474-9475; Dyck, L. E. (1989), *Life Sci.* 44, 1149-1156; Parker, E. M. and Cubeddu, L. X. (1988), *J. Pharmacol. Exp. Ther.* 245, 199-210. This view changed significantly with the recent identification of several members of a novel family of GPCRs, the trace amine associated receptors (TAARs). Lindemann, L. and Hoener, M. (2005), *Trends in Pharmacol. Sci.* 26, 274-281; Lindemann, L. et al. (2005), *Genomics* 85, 372-385.

There are 9 TAAR genes in human (including 3 pseudogenes) and 16 genes in mouse (including 1 pseudogene). The TAAR genes do not contain introns (with one exception, TAAR2 contains 1 intron) and are located next to each other on the same chromosomal segment. The phylogenetic relationship of the receptor genes, in agreement with an in-depth GPCR pharmacophore similarity comparison and pharmacological data suggest that these receptors form three distinct subfamilies. Lindemann, L. and Hoener, M. (2005), *Trends in Pharmacol. Sci.* 26, 274-281; Lindemann, L. et al. (2005), *Genomics* 85, 372-385. TAAR1 is in the first subclass of four genes (TAAR1-4) highly conserved between human and rodents. TAs activate TAAR1 via Gαs. Disregulation of TAs was shown to contribute to the aetiology of various diseases like depression, psychosis, attention deficit hyperactivity disorder, substance abuse, Parkinson's disease, migraine headache, eating disorders, metabolic disorders and therefore TAAR1 ligands have a high potential for the treatment of these diseases.

It has been found that the compounds of formula I (described below) have a good affinity to the TAARs, especially for TAAR1.

The compounds as useful in the treatment or prevention of depression, anxiety disorders, bipolar disorder, attention deficit hyperactivity disorder (ADHD), stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and/or cardiovascular disorders. Preferably, the compounds are useful in the treatment or prevention of disorders of the central nervous system, for example, the treatment or prevention of depression, psychosis, Parkinson's disease, anxiety and/or attention deficit hyperactivity disorder (ADHD).

SUMMARY OF THE INVENTION

The present invention relates to compounds of formula I,

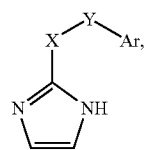

wherein
X is —CH$_2$— or —NH—;
Y is —CH(lower alkoxy)-, —CH(lower alkyl)-, —O—, —S—, —S(O)—, —S(O)$_2$— or —CH$_2$—; and
Ar is phenyl or naphthyl, which rings are optionally substituted by one or two substituents selected from the group consisting of halogen, lower alkoxy, lower alkyl and lower alkyl substituted by halogen;
with the proviso that, when X is —NH—, Y is —CH(lower alkyl)- or —CH$_2$—;
and the further proviso that the compound is not
2-phenethyl-1H-imidazole hydrochloride,
2-(3,4-dichloro-phenoxymethyl)-1H-imidazole hydrochloride,
2-(2-chloro-phenoxymethyl)-1H-imidazole hydrochloride,
2-(2,3-dichloro-phenoxymethyl)-1H-imidazole, benzyl-(1H-imidazol-2-yl)-amine,
(4-chloro-benzyl)-(1H-imidazol-2-yl)-amine, or
(2-chloro-benzyl)-(1H-imidazol-2-yl)-amine.

The invention relates also to a pharmaceutically-acceptable acid-addition salt of the above compound.

The present invention is also directed to a pharmaceutical composition comprising the above compound or a pharmaceutically-acceptable acid-addition salt thereof.

Compounds according to the present invention have a good affinity to the TAARs, especially for TAAR1. Such compounds are useful in the treatment or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders. Preferably, the compounds of the present invention are useful in the treatment or prevention of disorders of the central nervous system, for example, the treatment or prevention of depression, psychosis, Parkinson's disease, anxiety and attention deficit hyperactivity disorder (ADHD).

DETAILED DESCRIPTION OF THE INVENTION

The present invention relates to compounds of formula I,

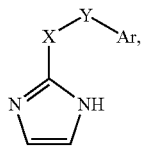

I wherein
X is —CH$_2$— or —NH—;
Y is —CH(lower alkoxy)-, —CH(lower alkyl)-, —O—, —S—, —S(O)—, —S(O)$_2$— or —CH$_2$—; and
Ar is phenyl or naphthyl, which rings are optionally substituted by one or two substituents selected from the group consisting of halogen, lower alkoxy, lower alkyl and lower alkyl substituted by halogen;
with the proviso that, when X is —NH—, Y is —CH(lower alkyl)- or —CH$_2$—;
and the further proviso that the compound is not
2-phenethyl-1H-imidazole hydrochloride,
2-(3,4-dichloro-phenoxymethyl)-1H-imidazole hydrochloride,
2-(2-chloro-phenoxymethyl)-1H-imidazole hydrochloride,
2-(2,3-dichloro-phenoxymethyl)-1H-imidazole,
benzyl-(1H-imidazol-2-yl)-amine,
(4-chloro-benzyl)-(1H-imidazol-2-yl)-amine, or
(2-chloro-benzyl)-(1H-imidazol-2-yl)-amine.

The invention relates also to a pharmaceutically-acceptable acid-addition salt of the above compound.

Such compounds have a good affinity to the TAARs, especially for TAAR1 and are useful in the treatment or prevention of illnesses such as depression, anxiety disorders, bipolar disorder, attention deficit hyperactivity disorder, stress-related disorders, psychotic disorders such as schizophrenia, neurological diseases such as Parkinson's disease, neurodegenerative disorders such as Alzheimer's disease, epilepsy, migraine, hypertension, substance abuse and metabolic disorders such as eating disorders, diabetes, diabetic complications, obesity, dyslipidemia, disorders of energy consumption and assimilation, disorders and malfunction of body temperature homeostasis, disorders of sleep and circadian rhythm, and cardiovascular disorders. Preferably, the compounds of the present invention are useful in the treatment or prevention of disorders of the central nervous system, for example, the treatment or prevention of depression, psychosis, Parkinson's disease, anxiety and attention deficit hyperactivity disorder (ADHD).

As used herein, the term "halogen" refers to chlorine, iodine, fluorine, or bromine.

As used herein, the term "lower alkyl" denotes a saturated straight- or branched-chain hydrocarbon group containing from 1 to 7 carbon atoms, for example, methyl, ethyl, propyl, isopropyl, n-butyl, i-butyl, 2-butyl, t-butyl and the like. Preferred lower alkyl groups are groups with 1 to 4 carbon atoms.

As used herein, the term "lower alkyl substituted by halogen" denotes a lower alkyl group as defined above, wherein at least one hydrogen atom is replaced by halogen, for example —CF$_3$, —CHF$_2$, —CH$_2$F, —CH$_2$CF$_3$, —CH$_2$CH$_2$CF$_3$, —CH$_2$CF$_2$CF$_3$ and the like.

As used herein, the term "lower alkoxy" denotes a substituent in which a lower alkyl group is attached to the remainder of the molecule via an oxygen atom.

The term "pharmaceutically-acceptable acid-addition salt" embraces salts of a compound of formula I with inorganic and organic acids, such as hydrochloric acid, nitric acid, sulfuric acid, phosphoric acid, citric acid, formic acid, fumaric acid, maleic acid, acetic acid, succinic acid, tartaric acid, methanesulfonic acid, p-toluenesulfonic acid and the like, the salt not being toxic and not interfering with the ability of the compound of formula I to elicit the biological or medical response of a tissue system, animal or human, that is being sought by the researcher, veterinarian, medical doctor or other clinician.

In a preferred embodiment, the compound of the present invention is a compound of formula I wherein X is —CH$_2$— or a pharmaceutically-acceptable acid-addition salt of such a compound. Examples of such compounds include:
2-[2-(3-chloro-phenyl)-2-methoxy-ethyl]-1H-imidazole;
2-(2,3-dichloro-phenylsulfanylmethyl)-1H-imidazole; and pharmaceutically-acceptable acid-addition salts of such compounds.

In another preferred embodiment, the compound is a compound of formula I wherein X is —NH— or a pharmaceutically-acceptable acid-addition salt of such a compound. Examples of such compounds include:
(3-chloro-benzyl)-(1H-imidazol-2-yl)-amine;
(3,4-dichloro-benzyl)-(1H-imidazol-2-yl)-amine;
(2,3-dichloro-benzyl)-(1H-imidazol-2-yl)-amine;
(R,S)-(1H-imidazol-2-yl)-(1-phenyl-ethyl)-amine;
(1H-imidazol-2-yl)-(3-methyl-benzyl)-amine;
(3-fluoro-benzyl)-(1H-imidazol-2-yl)-amine;
(R,S)-(1H-imidazol-2-yl)-(1-o-tolyl-ethyl)-amine;
(R,S)-[1-(2,3-dichloro-phenyl)-ethyl]-(1H-imidazol-2-yl)-amine;
(1H-imidazol-2-yl)-naphthalen-2-ylmethyl-amine;
(R,S)-[1-(2-chloro-phenyl)-ethyl]-(1H-imidazol-2-yl)-amine; and pharmaceutically-acceptable acid-addition salts of such compounds.

In a further preferred embodiment, the compound is a compound of formula wherein Y is —CH$_2$— or a pharmaceutically-acceptable acid-addition salt thereof. Examples of such compounds include:
(3-chloro-benzyl)-(1H-imidazol-2-yl)-amine;
(3,4-dichloro-benzyl)-(1H-imidazol-2-yl)-amine;
(2,3-dichloro-benzyl)-(1H-imidazol-2-yl)-amine;
(1H-imidazol-2-yl)-(3-methyl-benzyl)-amine;
(3-fluoro-benzyl)-(1H-imidazol-2-yl)-amine;
(1H-imidazol-2-yl)-naphthalen-2-ylmethyl-amine; and pharmaceutically-acceptable acid-addition salts of such compounds.

In a further preferred embodiment, the compound is a compound of formula I wherein Y is —CH(lower alkyl)- or —CH(lower alkoxy)- or a pharmaceutically-acceptable acid-addition salt thereof. Examples of such compounds include:
2-[2-(3-chloro-phenyl)-2-methoxy-ethyl]-1H-imidazole;
(R,S)-(1H-imidazol-2-yl)-(1-phenyl-ethyl)-amine;
(R,S)-(1H-imidazol-2-yl)-(1-phenyl-propyl)-amine;
(R,S)-(1H-imidazol-2-yl)-(1-o-tolyl-ethyl)-amine;
(R,S)-[1-(2,3-dichloro-phenyl)-ethyl]-(1H-imidazol-2-yl)-amine;
(R,S)-[1-(2-chloro-phenyl)-ethyl]-(1H-imidazol-2-yl)-amine; and pharmaceutically-acceptable acid-addition salts of such compounds.

In yet another preferred embodiment, the compound is a compound of formula I wherein Y is —O— or a pharmaceutically-acceptable acid-addition salt thereof. Examples of such compounds include:

2-(2,3-difluoro-phenoxymethyl)-1H-imidazole and a pharmaceutically-acceptable acid-addition salt thereof.

In yet another preferred embodiment, the compound is a compound of formula I wherein Y is —S—, S(O)— or —S(O)$_2$— or a pharmaceutically-acceptable acid-addition salt thereof. Examples of such compounds include:
2-(2,3-dichloro-phenylsulfanylmethyl)-1H-imidazole;
2-(2,3-dichloro-benzenesulfonylmethyl)-1H-imidazole;
2-(2,3-dichloro-benzenesulfonylmethyl)-1H-imidazole; and pharmaceutically-acceptable acid-addition salts of such compounds.

The present compounds of formula I and their pharmaceutically-acceptable acid-addition salts can be prepared by processes such as those described below as well as processes known in the art.

One such process comprises deprotecting a compound of formula II,

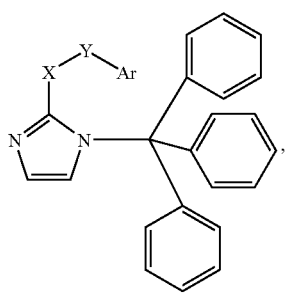

to form a compound of formula I. X, Y, and Ar are as described above.

The compound of formula II may be formed by various processes. In an embodiment in which the compound of formula II is one in which X is —CH$_2$— and Y is —C(OCH$_3$)H—, the compound may be formed by alkylating a compound according to formula V,

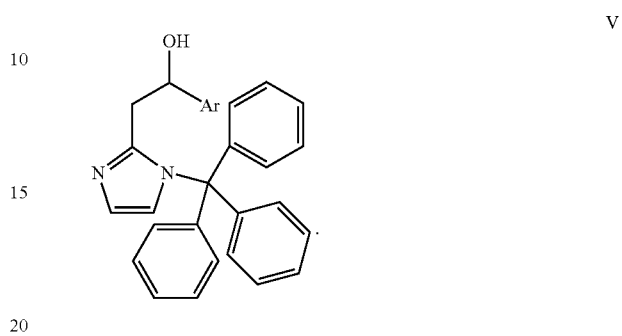

In an embodiment in which the compound of formula II is one in which X is —CH$_2$— and Y is —O—, the compound may be formed by reacting a compound of formula III-3,

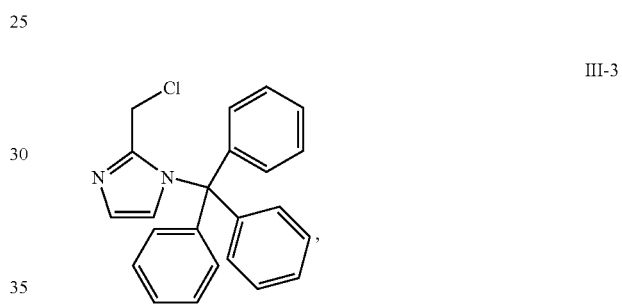

and a compound of formula IV-2,

In an embodiment in which the compound of formula II is one in which X is —CH$_2$— and Y is —S—, the compound may be formed by reacting a compound of formula III-3,

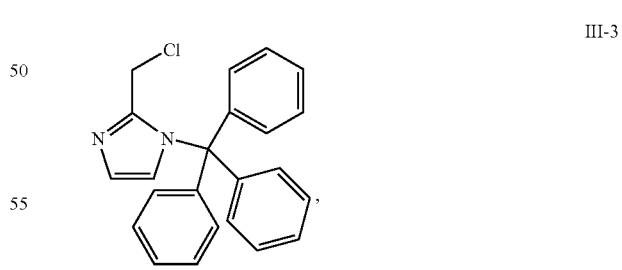

and a compound of formula IV-3,

In an embodiment in which X is —CH$_2$— and Y is —S(O)— or —S(O)$_2$—, the compound may be formed by oxidizing a compound of formula II-3,

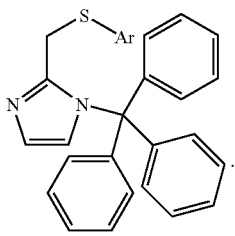

In another process, a compound according to formula I in which X is —NH— and Y is —C(R²)— wherein R² is hydrogen or lower alkyl, i.e., a compound according to formula I-6,

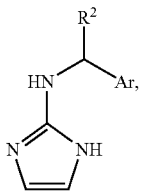

may be produced by reducing a compound of formula VI,

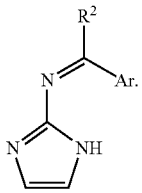

Ar is as defined above.

In yet another process, a compound according to formula I-6 in which R² is lower alkyl may be produced by reacting a compound according to formula VI-1,

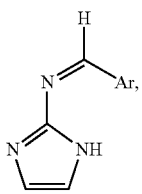

with a compound of formula R²MgHal, wherein Hal and Ar are as defined above. Preferred Hal is Br.

If desired the compound of formula I may be converted into a pharmaceutically-acceptable acid-addition salt.

The following are general schemes which exemplify the use of the above processes in the production of compounds of formula I. The starting materials are either commercially available (e.g., from one or more of the following chemical suppliers such as Aldrich, Fluka, Acros, Maybridge, Avocado, TCI, or additional suppliers as indicated in databases such as Chemical Abstracts [American Chemical Society, Columbus, Ohio] or Available Chemicals Director [Elsevier MDL, San Ramon, Calif.]), are otherwise known in the chemical literature, or may be prepared in accordance with methods well known in the art.

Procedure A

Synthesis of C—C-Linked Compounds

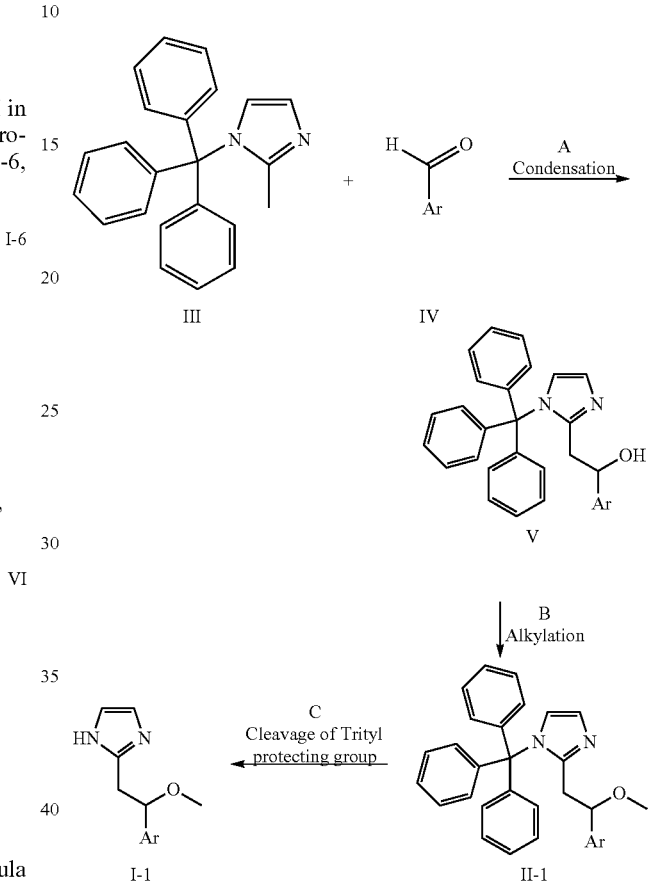

Scheme 1 describes the production of a compound of formula I in which X is —CH₂— and Y is —C(O)CH₃— (I-1). In the process, a compound of formula II in which X is —CH₂— and Y is —C(O)CH₃— (II-1) is deprotected.

Step A: The condensation between 2-methyl-1-tritylimidazole (III) can be effected by first deprotonating the 2-methyl-1-tritylimidazole with a base such as n-butyllithium, sec-butyllithium, tert-butyllithium or phenyl lithium optionally in the presence of a chelating amine such as tetramethyl ethylenediamine or pentamethyl diethylenetriamine in a solvent such as tetrahydrofuran (THF) or diethylether at −78° C.−−40° C. for 1-8 hrs and then reacting the anion in the same solvent with a corresponding aldehyde (IV) at −78° C. to room temperature. for 2-24 hrs.

Preferred conditions are deprotonation with n-butyllithium in the presence of pentamethyl diethylene triamine in THF at −78° C. for 6 hrs, then reaction with the compound of formula IV at −78° C.→room temperature overnight.

Step B: The alkylation of the alcohol (V) can be accomplished by deprotonation of the hydroxy group with a base such as NaH, KH, n-butyllithium, KO-tert-butyl, KOH or aqueous NaOH and KOH in the presence of a phase transfer catalyst (tetraalkylammonium salts) in a suitable solvent such as THF, dimethylformamide (DMF), dimethyl sulfoxide (DMSO), toluene or 1,2-dimethoxyethane at −78° C. to room temperature for 30 min-2 hrs and subsequent addition of an alkyl halide.

Preferred conditions are deprotonation with NaH in THF at room temperature for 1 hr and alkylation with an alkyl iodide at room temperature overnight.

Step C: The cleavage of the trityl group to obtain a compound of formula I-1 can be effected with a mineral acid such as HCl, $H_2SO_4$ or $H_3PO_4$ or a organic acid such as $CF_3COOH$, $CHCl_2COOH$, acetic acid or p-toluenesulfonic acid in a solvent such as $CH_2Cl_2$, $CHCl_3$, THF, methanol, ethanol or $H_2O$ at 0 to 60° C.

Preferred conditions are 2N HCl in ethanol at reflux for 1-3 hrs.

Procedure B

Synthesis of C—O-Linked Compounds

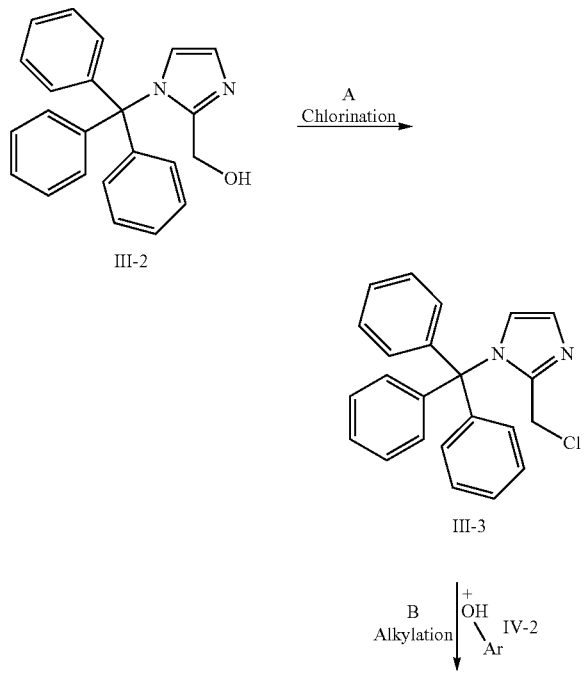

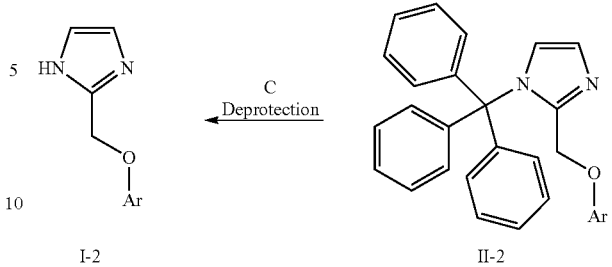

Scheme 2 describes the production of a compound of formula I in which X is —$CH_2$— and Y is —O— (I-2). In the process, a compound of formula II in which X is —$CH_2$— and Y is —O— (II-2) is deprotected.

Step A: The conversion of the alcohol (III-2) to the corresponding chloride (III-3) can be effected by the treatment with thionyl chloride, para-toluenesulfonyl chloride, methanesulfonylchloride, cyanuric chloride, $CCl_4$/triphenyl phosphine, aqueous or gaseous HCl and—if appropriate—in the presence of an organic base such as triethylamine or pyridine in a solvent such as toluene, benzene, dichloromethane, chloroform, dioxane, THF or diethylether at 0° C.-50° C. for 1-6 hrs.

Preferred conditions are treatment with thionyl chloride in the presence of triethylamine in toluene at 0° C. for 1 hr.

Step B: The alkylation of the compound of formula IV-2 with 2-chloromethyl-1-trityl-1H-imidazole (III-3) can be accomplished using a base such as $K_2CO_3$, $Cs_2CO_3$, $Na_2CO_3$, $NaHCO_3$, aqueous NaOH, KOH, LiOH, NaH, $NaOCH_3$, $NaOCH_2CH_3$ or triethylamine in a solvent such as acetone, DMF, DMSO, acetonitrile, toluene, ethanol, methanol and optionally if appropriate a phase transfer catalyst such as tetrabutylammonium bromide or an additive such as a crown ether, tetrabutylammonium iodide or potassium iodide at room temperature to 120° C. for 1-24 hrs.

Preferred conditions are $K_2CO_3$ in DMF at 80° C. for 5 hrs.

Step C: The cleavage of the trityl group to a compound of formula I-2 can be effected with a mineral acid such as HCl, $H_2SO_4$ or $H_3PO_4$ or a organic acid such as $CF_3COOH$, $CHCl_2COOH$, acetic acid or p-toluenesulfonic acid in a solvent such as $CH_2Cl_2$, $CHCl_3$, THF, methanol, ethanol or $H_2O$ at 0 to 60° C.

Preferred conditions are 2N HCl in ethanol at reflux for 1-3 hrs.

Procedure C

Synthesis of C—S-Linked Compounds

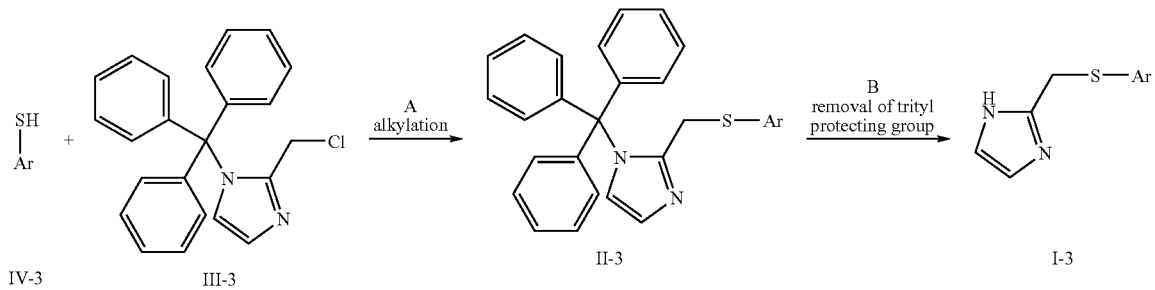

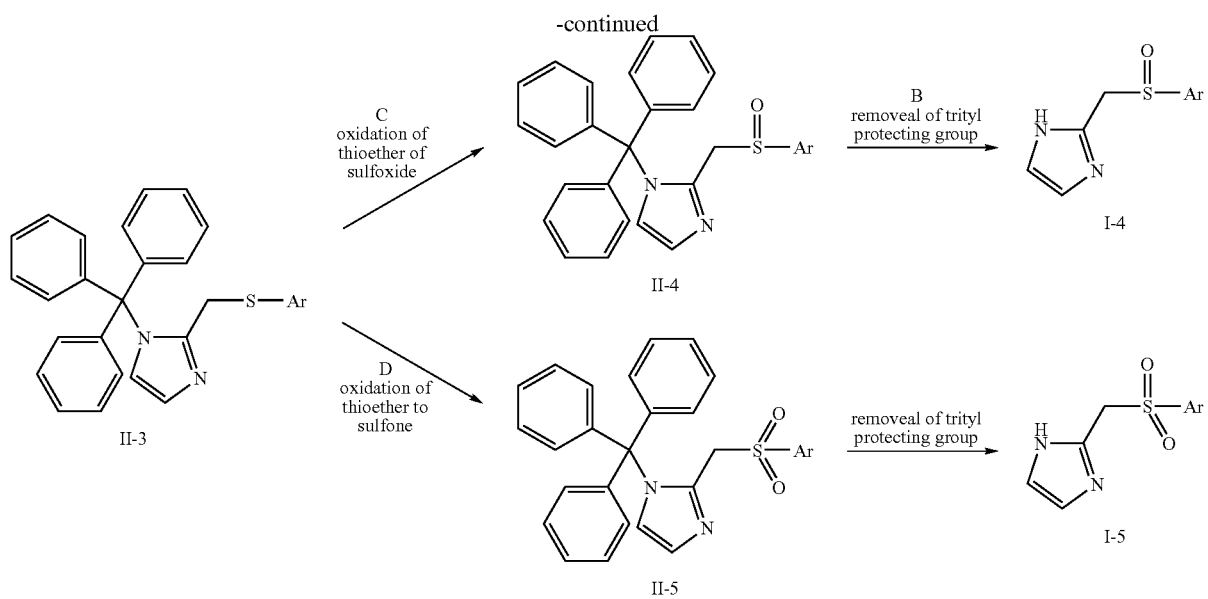

Scheme 3 describes the production of a compound of formula I in which X is —CH$_2$— and Y is —S— (I-3), a compound of formula I in which X is —CH$_2$— and Y is —S(O)—, and a compound of formula I in which X is —CH$_2$— and Y is —S(O)$_2$—.

In the process for the preparation of a compound of formula I-3, a compound of formula II in which X is —CH$_2$— and Y is —C(O)CH$_3$— (II-3) is deprotected.

Step A: The alkylation of IV-3 with 2-chloromethyl-1-trityl-1H-imidazole (III-3) can be accomplished using a base such as K$_2$CO$_3$, Cs$_2$CO$_3$, Na$_2$CO$_3$, NaHCO$_3$, aqueous NaOH, KOH, LiOH, NaH, NaOMe, NaOCH$_2$CH$_3$ or triethylamine in a solvent such as acetone, DMF, DMSO, acetonitrile, toluene, ethanol or methanol and optionally if appropriate a phase transfer catalyst such as tetrabutylammonium bromide or an additive such as a crown ether, tetrabutylammonium iodide or potassium iodide at room temperature to 120° C. for 1-24 hrs.

Preferred conditions are K$_2$CO$_3$ in DMF at 80° C. for 5 hrs.

Step B: The cleavage of the trityl group of compounds of formula II-3 can be effected with a mineral acid such as HCl, H$_2$SO$_4$ or H$_3$PO$_4$ or a organic acid such as CF$_3$COOH, CHCl$_2$COOH, HOAc or p-toluenesulfonic acid in a solvent such as CH$_2$Cl$_2$, CHCl$_3$, THF, methanol, ethanol or H$_2$O at 0 to 60° C.

Preferred conditions are 3N HCl in ethanol at reflux for 1-3 hrs.

If a compound of formula I in which Y is —S(O)— is desired, Step C may be used prior to Step B.

Step C: The oxidation of the thioether of formula II-3 to the corresponding sulfoxide (II-4) can be accomplished by oxidants such as meta-chloroperbenzoic acid (mCPBA), isopropyl 2-iodoxybenzoate, oxone or natriumperiodate in a solvent such as CH$_2$Cl$_2$, dichloroethane, toluene, acetonitrile, and methanol at temperatures from 0° C.-reflux.

Preferred conditions are 1 equivalent of mCPBA in CH$_2$Cl$_2$ at 0° C. to room temperature for 1-5 hrs.

If a compound of formula I in which Y is —S(O)$_2$— is desired, Step D may be used prior to Step B.

Step D: The oxidation of the thioether of formula II-3 to the corresponding sulfone (II-5) can be accomplished by oxidants such as mCPBA, H$_2$O$_2$ or oxone in a solvent such as CH$_2$Cl$_2$, dichloroethane, toluene, acetonitrile, THF, acetone, MeOH at temperatures from 0° C.-reflux.

Preferred conditions are 2 equivalent of mCPBA in CH$_2$Cl$_2$ at 0° C. to room temperature for 1-5 hrs.

Procedure D

Synthesis of N—C-Linked Compounds

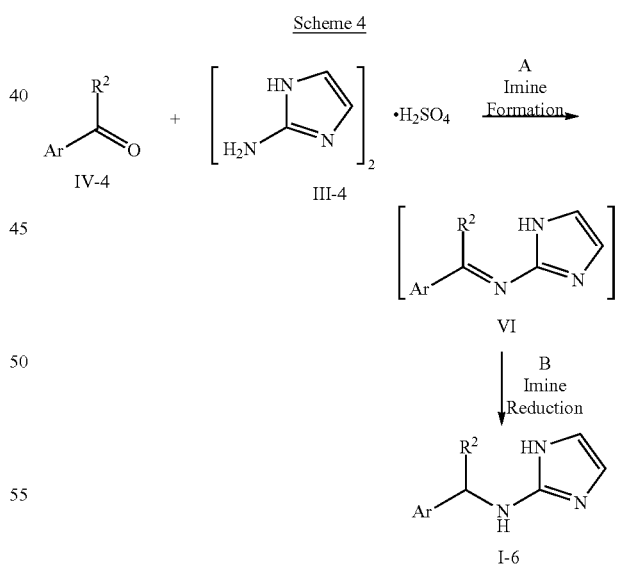

Scheme 4 describes the production of a compound of formula I in which X is —NH— and Y is —C(R$^2$)— wherein R$^2$ is hydrogen or lower alkyl (I-6).

Step A: The imine formation between an aryl aldehyde or an aryl ketone (IV-4) and 2-aminoimidazole sulfate (III-4) can be accomplished by Lewis acids such as Ti(OiPr)$_4$ or ZnCl$_2$ in combination with organic bases such as triethylamine or ethyldiisopropylamine in chlorinated organic solvents such as dichloromethane or 1,2-dichloroethane at room temperature or at an elevated temperature such as the reflux temperature of the solvent.

In the case where an aryl aldehyde is used, preferred conditions are Ti(OiPr)$_4$ and triethylamine in dichloromethane at room temperature for around 16 hrs. In the case where an aryl ketone is used, preferred conditions are Ti(OiPr)$_4$ and triethylamine in 1,2-dichloroethane at reflux for around 16 hrs.

Step B: The imine reduction to afford the corresponding amine of formula I-6 can be accomplished using a metal hydride reducing agent such as sodium borohydride in an alcoholic solvent such as ethanol or methanol, or by using a metal hydride reducing agent such as lithium borohydride or lithium aluminium hydride in an ethereal solvent such as diethyl ether, dioxane or tetrahydrofuran, at room temperature or at an elevated temperature such as the reflux temperature of the solvent.

Preferred conditions are sodium borohydride in ethanol at room temperature for around 2-4 hrs.

Procedure E

Alternative Synthesis of N—C-Linked Compounds

Scheme 5

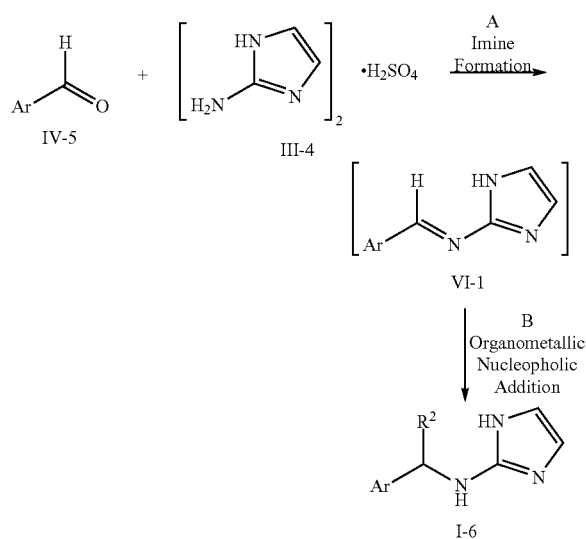

Scheme 4 describes the production of a compound of formula I in which X is —NH— and Y is —C(R$^2$)— wherein R$^2$ is lower alkyl (1-6).

Step A: The imine formation between an aryl aldehyde (IV-5) and 2-aminoimidazole sulfate (III-4) can be accomplished by Lewis acids such as Ti(OiPr)$_4$ or ZnCl$_2$ in combination with organic bases such as triethylamine or ethyldiisopropylamine in chlorinated organic solvents such as dichloromethane or 1,2-dichloroethane at room temperature or at an elevated temperature such as the reflux temperature of the solvent.

Preferred conditions are Ti(OiPr)$_4$ and triethylamine in dichloromethane at room temperature for around 16 hrs.

Step B: The nucleophilic addition of an organometallic agent to an imine to afford an amine compound of formula I-6 can be accomplished using a Grignard reagent or an organolithium reagent in the presence of a Lewis acid catalyst such as scandium triflate in an ethereal solvent such as diethyl ether, dioxane or tetrahydrofuran, or a hydrocarbon solvent such as toluene, at room temperature or at an elevated temperature such as the reflux temperature of the solvent.

Preferred conditions are alkylmagenisum bromide and scandium triflate in a mixture of ether and toluene at room temperature for around 2 hrs.

Isolation and Purification of the Compounds

Isolation and purification of the compounds and intermediates described herein can be effected, if desired, by any suitable separation or purification procedure such as, for example, filtration, extraction, crystallization, column chromatography, thin-layer chromatography, thick-layer chromatography, preparative low or high-pressure liquid chromatography or a combination of these procedures. Specific illustrations of suitable separation and isolation procedures can be had by reference to the preparations and examples herein below. However, other equivalent separation or isolation procedures could, of course, also be used. Racemic mixtures of chiral compounds of formula I can be separated using chiral HPLC.

Salts of Compounds of Formula I

The compounds of formula I are basic and may be converted to a corresponding acid-addition salt. The conversion is accomplished by treatment with at least a stoichiometric amount of an appropriate acid, such as hydrochloric acid, hydrobromic acid, sulfuric acid, nitric acid, phosphoric acid and the like, and organic acids such as acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid and the like. Typically, the free base is dissolved in an inert organic solvent such as diethyl ether, ethyl acetate, chloroform, ethanol or methanol and the like, and the acid added in a similar solvent. The temperature is maintained between 0° C. and 50° C. The resulting salt precipitates spontaneously or may be brought out of solution with a less polar solvent.

The acid-addition salts of the basic compounds of formula I may be converted to the corresponding free bases by treatment with at least a stoichiometric equivalent of a suitable base such as sodium or potassium hydroxide, potassium carbonate, sodium bicarbonate, ammonia, and the like.

The compounds of formula I and their pharmaceutically-acceptable acid-addition salts possess valuable pharmacological properties. Specifically, it has been found that the compounds of the present invention have a good affinity to the trace amine associated receptors (TAARs), especially TAAR1.

Another aspect of the present invention is a pharmaceutical composition comprising a compound of formula I, or a pharmaceutically-acceptable acid-addition salt thereof, and a therapeutically-inert carrier. Processes for the production of such a composition are also aspects of the present invention. Such a process comprises bringing one or more compounds of formula I and/or a pharmaceutically-acceptable salt(s) thereof and, if desired, one or more other therapeutically-valuable substances into a galenical administration form together with one or more therapeutically-inert carriers.

The term "therapeutically-inert carrier" means that the carrier is not toxic and does not interfere with the ability of the active compound(s) to elicit the biological or medical response of a tissue system, animal or human that is being sought by the researcher, veterinarian, medical doctor or other clinician. The therapeutically-inert carrier for use in the composition of the present invention may be inorganic or organic. Lactose, corn starch or derivatives thereof, talc, stearic acids or its salts and the like can be used, for example, as such carriers for tablets, coated tablets, dragées and hard gelatine capsules. Suitable carriers for soft gelatine capsules are, for example, vegetable oils, waxes, fats, semi-solid and liquid polyols and the like. Depending on the nature of the active substance, no carriers are however usually required in the case of soft gelatine capsules. Suitable carriers for the production of solutions and syrups are, for example, water, polyols, glycerol, vegetable oil and the like. Suitable carriers for suppositories are, for example, natural or hardened oils, waxes, fats, semi-liquid or liquid polyols and the like.

The pharmaceutical composition can, moreover, contain preservatives, solubilizers, stabilizers, wetting agents, emulsifiers, sweeteners, colorants, flavorants, salts for varying the osmotic pressure, buffers, masking agents and antioxidants. The composition can also contain still other therapeutically valuable substances.

The pharmaceutical composition of the present invention can be administered orally, e.g. in the form of tablets, coated tablets, dragées, hard and soft gelatine capsules, solutions, emulsions or suspensions. The administration can, however, also be effected rectally, e.g. in the form of suppositories, parenterally, e.g. in the form of injection solutions.

The present invention relates also to a method for treating or preventing a disease or disorder in a patient comprising administering a therapeutically-effective amount of a compound of the present invention to a patient. A "therapeutically-effective amount" is the amount of the subject compound that will elicit the biological or medical response of a tissue system, animal or human, that is being sought by the researcher, veterinarian, medical doctor or other clinician. The above method may involve the administration of a composition which comprises a therapeutically-effective amount of the compound such as the composition described above.

The therapeutically-effective amount can vary within wide limits and will, of course, have to be adjusted to the individual requirements in each particular case. In the case of oral administration the dosage for adults can vary from about 0.01 mg to about 1000 mg per day of a compound of general formula I or of the corresponding amount of a pharmaceutically-acceptable acid-addition salt thereof. The daily dosage may be administered as single dose or in divided doses and, in addition, the upper limit can also be exceeded when this is found to be indicated.

EXAMPLES

The following examples illustrate the invention but are not intended to limit its scope.

Example 1

2-[2-(3-Chloro-phenyl)-2-methoxy-ethyl]-1H-imidazole a) 1-(3-Chloro-phenyl)-2-(1-trityl-1H-imidazol-2-yl)-ethanol

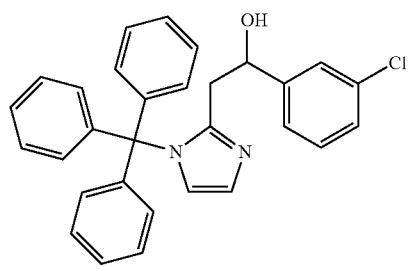

To a stirred, cooled (−78° C., acetone/dry ice bath) solution of 2-methyl-1-tritylimidazole (1 g; CAS 23593-68-2) in tetrahydrofuran (THF) (15 ml) under an argon atmosphere was added pentamethyldiethylene-triamine (0.64 ml). n-butyl-lithium solution (2.0 ml; 1.6 M in hexanes) was then added dropwise over a period of 10 min. The reaction mixture soon turned to a dark red compact slurry. The mixture was then stirred at a temperature between −40° C. and −50° C. for 6 hours. After cooling again to −78° C., a solution of 3-chlorobenzaldehyde (0.86 g) in THF (5 ml) was added dropwise for 5 minutes. The mixture was stirred overnight, slowly warming up to room temperature. The clear yellow solution was diluted with ethyl acetate (30 ml) and washed with $H_2O$. The aqueous phase was back extracted with ethyl acetate (EtOAc). The combined organics were washed with $H_2O$ and brine, dried over $MgSO_4$, filtered and concentrated. The crude product was purified by column chromatography (silica gel; gradient $CH_2Cl_2 \rightarrow CH_2Cl_2$/methanol 92:8) to give 1-(3-chloro-phenyl)-2-(1-trityl-1H-imidazol-2-yl)-ethanol (1.04 g) as light yellow amorphous solid. MS (ISP): 243.3 ([Trt]$^+$)

b) 2-[2-(3-Chloro-phenyl)-2-methoxy-ethyl]-1-trityl-1H-imidazole

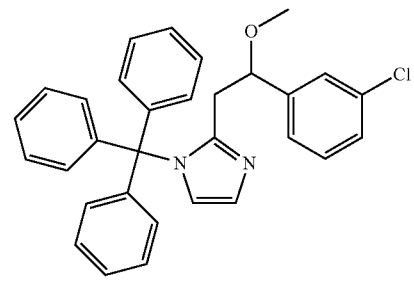

To a stirred solution of 1-(3-chloro-phenyl)-2-(1-trityl-1H-imidazol-2-yl)-ethanol (0.34 g) at room temperature in THF (5 ml) under an argon atmosphere was added NaH (33 mg; 55% dispersion in mineral oil) in one portion. After 1 hour stirring at room temperature, methyl iodide (0.07 ml) was added and stirring at room temperature was continued for 17 hours.

The mixture was diluted with EtOAc and washed with $H_2O$. The aqueous phase was back extracted with EtOAc. The combined organics were washed with $H_2O$ and brine, dried over $MgSO_4$, filtered and concentrated. The crude product was isolated by column chromatography (silica gel; gradient: cyclohexane→cyclohexane/EtOAc 1:1) to give 2-[2-(3-chloro-phenyl)-2-methoxy-ethyl]-1-trityl-1H-imidazole (0.25 g) as light yellow amorphous solid. MS 479.0 ([M+H]$^+$)

c) 2-[2-(3-Chloro-phenyl)-2-methoxy-ethyl]-1H-imidazole

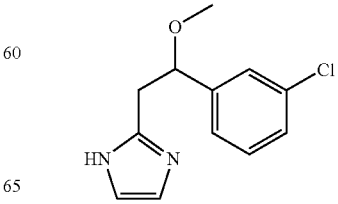

To a stirred suspension of 2-[2-(3-chloro-phenyl)-2-methoxy-ethyl]-1-trityl-1H-imidazole (0.24 g) at room temperature in ethanol (2 ml) under an argon atmosphere was added 2 N HCl (3 ml). The mixture was heated to reflux. Stirring was continued for 3 hours. The mixture was cooled to room temperature and concentrated to leave a light yellow solid. This was taken up in H$_2$O and brought to pH=12 by the addition of 4 N NaOH. The product was extracted with CH$_2$Cl$_2$/methanol 4:1. The combined organics were dried over MgSO$_4$, filtered and concentrated. The crude product was purified by column chromatography (silica gel; gradient:CH$_2$Cl$_2$→CH$_2$Cl$_2$/methanol 9:1) to give 2-[2-(3-chloro-phenyl)-2-methoxy-ethyl]-1H-imidazole (0.11 mg) as light yellow gum. MS 237.1 ([M+H]$^+$)

Example 2

2-(2,3-Difluoro-phenoxymethyl)-1H-imidazole a) 2-Chloromethyl-1-trityl-1H-imidazole

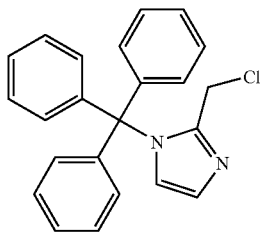

A suspension of (1-trityl-1H-imidazol-2-yl)-methanol (9.92 g; CAS 102152-03-4) in toluene (160 ml) was cooled under an argon atmosphere to 0° C. and treated with triethylamine (8.1 ml). Then, thionylchloride (2.96 ml) was added dropwise. The reaction mixture was stirred for 1 hour at 0° C., then treated with 500 ml ice-cold H$_2$O. The mixture was extracted with EtOAc. The organic layer was washed with H$_2$O, dried over MgSO$_4$ and concentrated. The crude product was purified by column chromatography (silica gel; eluent: CH$_2$Cl$_2$/methanol 95:5) to give 2-chloromethyl-1-trityl-1H-imidazole (2.73 g) as off-white solid. MS 359.0 ([M+H]$^+$)

b) 2-(2,3-Difluoro-phenoxymethyl)-1-trityl-1H-imidazole

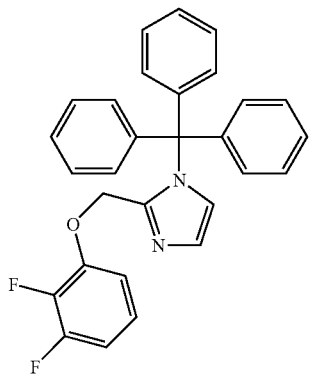

To a stirred solution of 2,3-difluorophenol (109 mg) at room temperature in dimethylformamide DMF (5 ml) under an argon atmosphere were added 2-chloromethyl-1-trityl-1H-imidazole (200 mg) and potassium carbonate (193 mg). The mixture was heated to 80° C. and stirring was continued overnight. The brown suspension was cooled to room temperature, diluted with EtOAc and washed with 1 N NaOH. The aqueous phase was back extracted with EtOAc. The combined organics were washed with H$_2$O and brine, dried over MgSO$_4$, filtered and concentrated. The crude product was purified by column chromatography (silica gel; gradient: cyclohexane→cyclohexane/EtOAc 55:45) to give 2-(2,3-difluoro-phenoxymethyl)-1-trityl-1H-imidazole (240 mg) as a light yellow gum. MS (ISP): 453.0 ([M+H]$^+$)

c) 2-(2,3-Difluoro-phenoxymethyl)-1H-imidazole

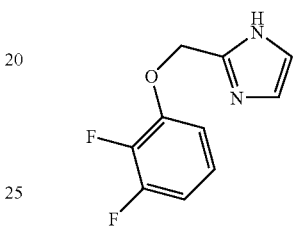

To a stirred suspension of 2-(2,3-difluoro-phenoxymethyl)-1-trityl-1H-imidazole (230 mg) at room temperature in ethanol (2 ml) under an argon atmosphere was added 2 N HCl (3 ml). The mixture was heated to reflux and stirring was continued for 5 hours. The reaction mixture was cooled to room temperature and concentrated to leave an off-white solid. This was taken up in sat. aq. Na$_2$CO$_3$ and extracted with CH$_2$Cl$_2$/methanol 9:1. The combined organics were dried over MgSO$_4$, filtered and concentrated. The crude product was purified by column chromatography (silica gel; gradient: CH$_2$Cl$_2$→CH$_2$Cl$_2$/methanol 9:1) to give 2-(2,3-difluoro-phenoxymethyl)-1H-imidazole (108 mg) as an off-white solid. MS 210.9 ([M+H]$^+$)

Example 3

2-(2,3-Dichloro-phenylsulfanylmethyl)-1H-imidazole a) 2-(2,3-Dichloro-phenylsulfanylmethyl)-1-trityl-1-imidazole

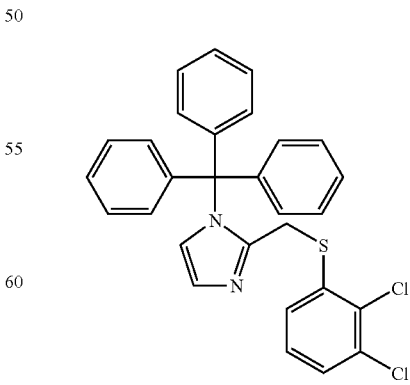

In analogy to example 2(b) 2-chloromethyl-1-trityl-1H-imidazole was reacted with 2,3-dichlorobenzenethiol to give 2-(2,3-dichloro-phenylsulfanylmethyl)-1-trityl-1-imidazole as an off-white solid. MS (ISP): 243.3 ([Trt]$^+$)

b)
2-(2,3-Dichloro-phenylsulfanylmethyl)-1H-imidazole

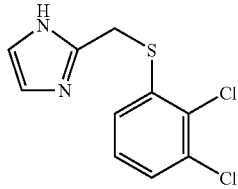

A solution of 2-(2,3-dichloro-phenylsulfanylmethyl)-1-trityl-1-imidazole (100 mg) in ethanol (4 ml) was treated with 3N HCl (4 ml) and heated to 100° C. for 3 hours. The reaction mixture was concentrated and taken up in water. The solution was made basic by the addition of K$_2$CO$_3$ and then extracted with CH$_2$Cl$_2$/methanol 4:1. The combined organics were dried over MgSO$_4$, filtered and concentrated. The crude product was purified by column chromatography (silica gel; gradient:CH$_2$Cl$_2$→CH$_2$Cl$_2$/MeOH 95:5) to give 2-(2,3-dichloro-phenylsulfanylmethyl)-1H-imidazole (48 mg) as a white solid.

Example 4

2-(2,3-Dichloro-benzenesulfonylmethyl)-1H-imidazole a) 2-(2,3-Dichloro-benzenesulfonylmethyl)-1-trityl-1H-imidazole

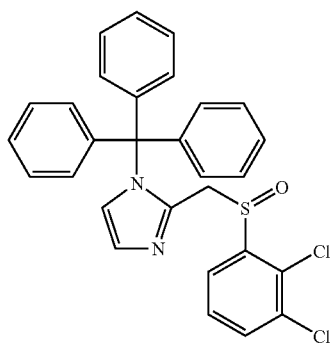

A solution of 2-(2,3-dichloro-phenylsulfanylmethyl)-1-trityl-1-imidazole (260 mg; produced in example 3(a)) in CH$_2$Cl$_2$/methanol was cooled to 0° C. and treated under an argon atmosphere with meta-chloro perbenzoic acid (89 mg). The reaction mixture was stirred for 20 hours at room temperature, then diluted with CH$_2$Cl$_2$ and washed with 1N NaOH. The organic layer was dried over MgSO$_4$, filtered and concentrated. The crude product was purified by column chromatography to give 2-(2,3-dichloro-benzenesulfonylmethyl)-1-trityl-1H-imidazole (204 mg) as a white solid. MS 517.3 ([M+H]$^+$)

b) 2-(2,3-Dichloro-benzenesulfonylmethyl)-1H-imidazole

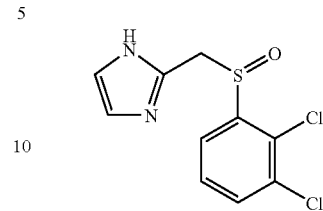

In analogy to example 3(b) 2-(2,3-dichloro-benzenesulfonylmethyl)-1-trityl-1H-imidazole was converted to 2-(2,3-dichloro-benzenesulfonylmethyl)-1H-imidazole. White solid. MS 275.0 ([M+H]$^+$)

Example 5

2-(2,3-Dichloro-benzenesulfonylmethyl)-1H-imidazole

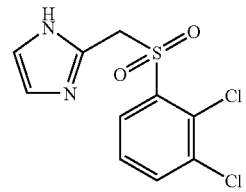

A solution of 2-(2,3-dichloro-phenylsulfanylmethyl)-1-trityl-1-imidazole (260 mg; produced in example 3(a)) in CH$_2$Cl$_2$/methanol was cooled to 0° C. and treated under an argon atmosphere with meta-chloro perbenzoic acid (448 mg). The reaction mixture was stirred for 2 days at room temperature, then diluted with CH$_2$Cl$_2$ and washed with 1N NaOH. The organic layer was dried over MgSO$_4$, filtered and concentrated. The crude product was purified by column chromatography to give 2-(2,3-dichloro-benzenesulfonylmethyl)-1H-imidazole (6 mg) as white solid. MS (ISP): 291.0 ([M+H]$^+$)

Example 6

(3-Chloro-benzyl)-(1H-imidazol-2-yl)-amine

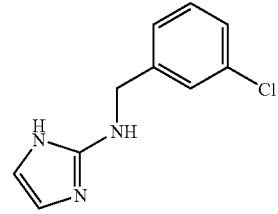

To a solution of 3-chlorobenzaldehyde (0.16 ml, 1.4 mmol) in dichloromethane (10 ml) were added sequentially 2-aminoimidazole sulfate (0.19 g, 0.7 mmol), tetraisopropyl orthotitanate (0.51 ml, 1.7 mmol) and triethylamine (0.19 ml, 1.4 mmol). The reaction mixture was stirred at room temperature for 16 hours and then concentrated in vacuo. The residue was taken up in ethanol (5 ml) and then sodium borohydride (54 mg, 1.4 mmol) was added. The reaction mixture was stirred at room temperature for 3 hours and then quenched by the addition of water. After stirring for a further 15 minutes at room temperature, the reaction mixture was filtered and the filter cake washed with ethanol. The filtrate was concentrated in vacuo and the residue was purified by chromatography on silica gel (eluant:methanol/dichloromethane 0:100 to 10:90) to yield the title compound as an off-white solid (87 mg, 30%); MS (ISP): 208.7 ([M+H]$^+$).

Example 7

(3,4-Dichloro-benzyl)-(1H-imidazol-2-yl)-amine

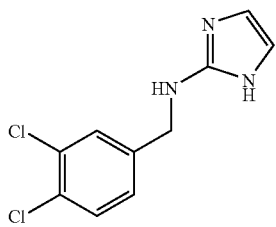

Analogously to Example 6, the title compound was obtained from 3,4-dichlorobenzaldehyde, 2-aminoimidazole sulfate, tetraisopropyl orthotitanate and triethylamine in dichloromethane and treatment with sodium borohydride in ethanol. MS (ISP): 246.1 ([{$^{37}$Cl}M+H]$^+$), 244.1 ([{$^{37}$Cl, $^{35}$Cl}M+H]$^+$), 242.1 ([{$^{35}$Cl}M+H]$^+$).

Example 8

(2,3-Dichloro-benzyl)-(1H-imidazol-2-yl)-amine

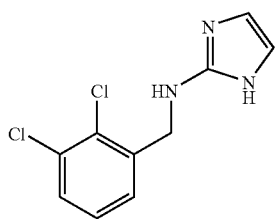

Analogously to Example 6, the title compound was obtained from 2,3-dichlorobenzaldehyde, 2-aminoimidazole sulfate, tetraisopropyl orthotitanate and triethylamine in dichloromethane and treatment with sodium borohydride in ethanol. MS (ISP): 246.1 ([{$^{37}$Cl}M+H]$^+$), 244.1 ([{$^{37}$Cl, $^{35}$Cl}M+H]$^+$), 242.1 ([{$^{35}$Cl}M+H]$^+$).

Example 9

(R,S)-(1H-Imidazol-2-yl)-(1-phenyl-ethyl)-amine

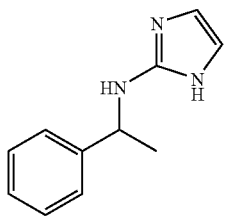

To a solution of acetophenone (0.19 ml, 1.63 mmol) in 1,2-dichloroethane (5 ml) were added sequentially 2-aminoimidazole sulfate (0.22 g, 0.84 mmol), tetraisopropyl orthotitanate (0.60 ml, 2.05 mmol) and triethylamine (0.23 ml, 1.66 mmol). The reaction mixture was stirred at 90° C. for 6 hours and then concentrated in vacuo. The residue was taken up in ethanol (5 ml) and then sodium borohydride (64 mg, 1.69 mmol) was added. The reaction mixture was stirred at room temperature for 2 hours and then quenched by the addition of water. After stirring for a further 15 minutes at room temperature, the reaction mixture was filtered and the filter cake washed with ethanol. The filtrate was concentrated in vacuo and the residue was purified by chromatography on silica gel (eluant:methanol/dichloromethane 0:100 to 10:90) to yield the title compound as a brown gum (30 mg, 10%); MS (ISP): 188.4 ([M+H]$^+$).

Example 10

(1H-Imidazol-2-yl)-(4-methoxy-benzyl)-amine

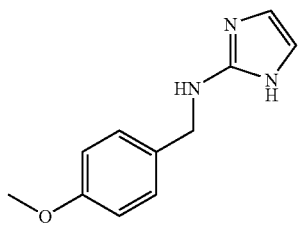

Analogously to Example 6, the title compound was obtained from 4-methoxybenzaldehyde, 2-aminoimidazole sulfate, tetraisopropyl orthotitanate and triethylamine in dichloromethane and treatment with sodium borohydride in ethanol. MS (ISP): 204.3 ([M+H]$^+$).

Example 11

(1H-Imidazol-2-yl)-(3-methyl-benzyl)-amine

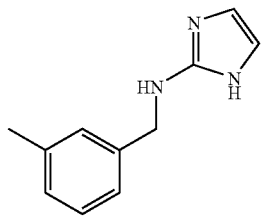

Analogously to Example 6, the title compound was obtained from 3-methylbenzaldehyde, 2-aminoimidazole sulfate, tetraisopropyl orthotitanate and triethylamine in dichloromethane and treatment with sodium borohydride in ethanol. MS (ISP): 188.4 ([M+H]$^+$).

Example 12

(2-Fluoro-benzyl)-(1H-imidazol-2-yl)-amine

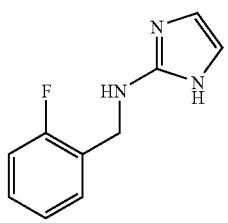

Analogously to Example 6, the title compound was obtained from 2-fluorobenzaldehyde, 2-aminoimidazole sulfate, tetraisopropyl orthotitanate and triethylamine in dichloromethane and treatment with sodium borohydride in ethanol. MS (ISP): 192.3 ([M+H]$^+$).

Example 13

(1H-Imidazol-2-yl)-(4-methyl-benzyl)-amine

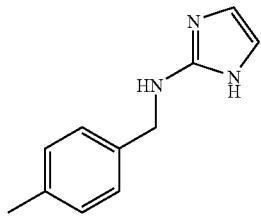

Analogously to Example 6, the title compound was obtained from 4-methylbenzaldehyde, 2-aminoimidazole sulfate, tetraisopropyl orthotitanate and triethylamine in dichloromethane and treatment with sodium borohydride in ethanol. MS (ISP): 188.4 ([M+H]$^+$).

Example 14

(1H-Imidazol-2-yl)-(3-methoxy-benzyl)-amine

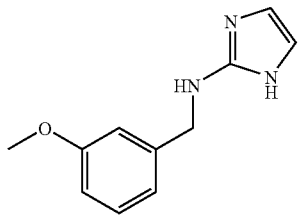

Analogously to Example 6, the title compound was obtained from 3-methoxybenzaldehyde, 2-aminoimidazole sulfate, tetraisopropyl orthotitanate and triethylamine in dichloromethane and treatment with sodium borohydride in ethanol. MS (ISP): 204.1 ([M+H]$^+$).

Example 15

(1H-Imidazol-2-yl)-(2-methoxy-benzyl)-amine

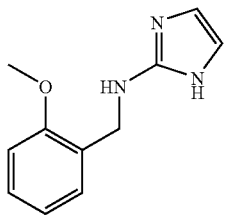

Analogously to Example 6, the title compound was obtained from 2-methoxybenzaldehyde, 2-aminoimidazole sulfate, tetraisopropyl orthotitanate and triethylamine in dichloromethane and treatment with sodium borohydride in ethanol. MS (ISP): 204.3 ([M+H]$^+$).

Example 16

(3-Fluoro-benzyl)-(1H-imidazol-2-yl)-amine

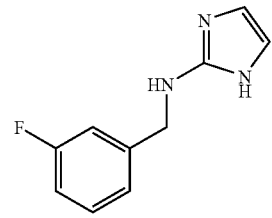

Analogously to Example 6, the title compound was obtained from 3-fluorobenzaldehyde, 2-aminoimidazole sulfate, tetraisopropyl orthotitanate and triethylamine in dichloromethane and treatment with sodium borohydride in ethanol. MS (ISP): 192.3 ([M+H]$^+$).

Example 17

(1H-Imidazol-2-yl)-(2-methyl-benzyl)-amine

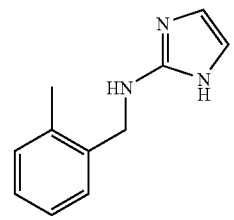

Analogously to Example 6, the title compound was obtained from 2-methylbenzaldehyde, 2-aminoimidazole sulfate, tetraisopropyl orthotitanate and triethylamine in dichloromethane and treatment with sodium borohydride in ethanol. MS (ISP): 188.4 ([M+H]$^+$).

Example 18

(1H-Imidazol-2-yl)-(3-trifluoromethyl-benzyl)-amine

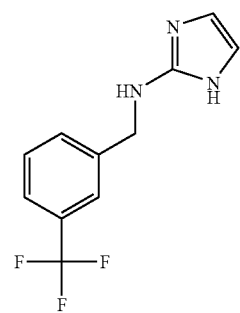

Analogously to Example 6, the title compound was obtained from 3-(trifluoromethyl)benzaldehyde, 2-aminoimidazole sulfate, tetraisopropyl orthotitanate and triethylamine in dichloromethane and treatment with sodium borohydride in ethanol. MS (ISP): 242.3 ([M+H]+).

Example 19

(2,6-Dimethyl-benzyl)-(1H-imidazol-2-yl)-amine

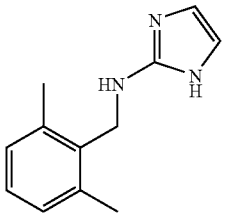

Analogously to Example 6, the title compound was obtained from 2,6-dimethylbenzaldehyde, 2-aminoimidazole sulfate, tetraisopropyl orthotitanate and triethylamine in dichloromethane and treatment with sodium borohydride in ethanol. MS (ISP): 202.4 ([M+H]+).

Example 20

(RS)-(1H-Imidazol-2-yl)-(1-phenyl-propyl)-amine

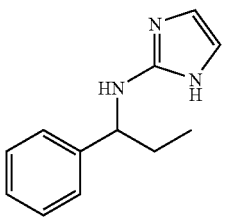

a) (1H-Imidazol-2-yl)-[1-phenyl-meth-(E)-ylidene]-amine

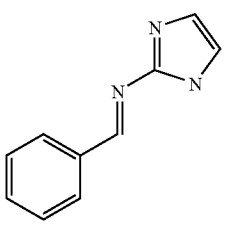

To a solution of benzaldehyde (1.92 ml, 18.8 mmol) in dichloromethane (15 ml) were added sequentially 2-aminoimidazole sulfate (3.77 g, 14.3 mmol), tetraisopropyl orthotitanate (6.83 ml, 23.3 mmol) and triethylamine (3.90 ml, 2.81 mmol). The reaction mixture was stirred at room temperature for 16 hours and then concentrated in vacuo. The residue was taken up in ethyl acetate and water and the mixture filtered. The filtrate phases were separated and the organic phase dried over sodium sulfate and concentrated in vacuo to yield the title compound as a yellow solid which was used in the next step without further purification (3.03 g, 95%); MS (ISP): 172.1 ([M+H]+).

b) (RS)-(1H-Imidazol-2-yl)-(1-phenyl-propyl)-amine

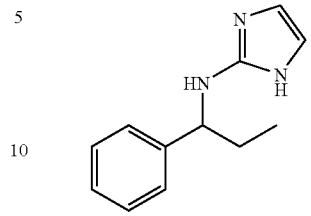

To a solution of (1H-imidazol-2-yl)-[1-phenyl-meth-(E)-ylidene]-amine (0.19 ml, 1.63 mmol) in toluene (6 ml) was added scandium triflate (59 mg, 0.12 mmol). An ethereal solution of ethylmagnesium bromide (0.97 ml, 3 M, 2.91 mmol) was then added dropwise and the reaction mixture was stirred at room temperature for 2 hours and then quenched by the addition of saturated aqueous ammonium chloride solution. The mixture was extracted twice with ether and the organic phases were dried over sodium sulfate and concentrated in vacuo. The residue was purified by chromatography on silica gel (eluant:methanol/dichloromethane 0:100 to 10:90) to yield the title compound as a brown gum (67 mg, 29%); MS (ISP): 202.4 ([M+H]+).

Example 21

(R,S)-(1H-Imidazol-2-yl)-(1-o-tolyl-ethyl)-amine

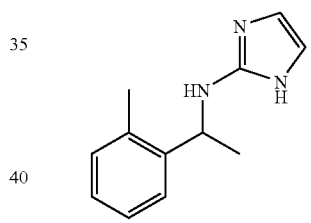

Analogously to Example 9, the title compound was obtained from 2-methylacetophenone, 2-aminoimidazole sulfate, tetraisopropyl orthotitanate and triethylamine in dichloromethane and treatment with sodium borohydride in ethanol. MS (ISP): 202.3 ([M+H]+).

Example 22

(R,S)-[1-(2,3-Dichloro-phenyl)-ethyl]-(1H-imidazol-2-yl)-amine

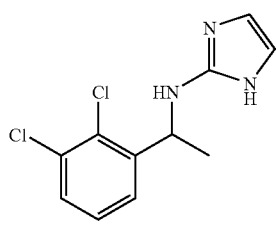

Analogously to Example 9, the title compound was obtained from 2,3-dichloroacetophenone, 2-aminoimidazole sulfate, tetraisopropyl orthotitanate and triethylamine in dichloromethane and treatment with sodium borohydride in ethanol. MS (ISP): 260.1 ([$\{^{37}Cl\}M+H$]$^+$), 258.0 ([$\{^{37}Cl^{35}Cl\}M+H$]$^+$), 256.2 ([$\{^{35}Cl\}M+H$]$^+$).

Example 23

(1H-Imidazol-2-yl)-naphthalen-1-ylmethyl-amine

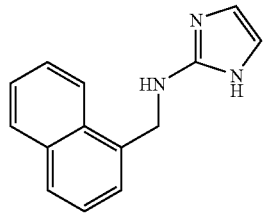

Analogously to Example 6, the title compound was obtained from 1-naphtaldehyde, 2-aminoimidazole sulfate, tetraisopropyl orthotitanate and triethylamine in dichloromethane and treatment with sodium borohydride in ethanol. MS (ISP): 224.3 ([M+H]$^+$).

Example 24

(1H-Imidazol-2-yl)-naphthalen-2-ylmethyl-amine

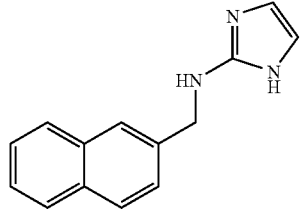

Analogously to Example 6, the title compound was obtained from 2-naphthaldehyde, 2-aminoimidazole sulfate, tetraisopropyl orthotitanate and triethylamine in dichloromethane and treatment with sodium borohydride in ethanol. MS (ISP): 224.3 ([M+H]$^+$).

Example 25

(2,6-Dichloro-benzyl)-(1H-imidazol-2-yl)-amine

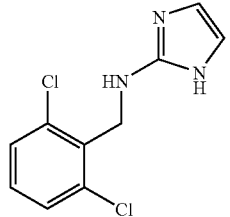

Analogously to Example 6, the title compound was obtained from 2,6-dichlorobenzaldehyde, 2-aminoimidazole sulfate, tetraisopropyl orthotitanate and triethylamine in dichloromethane and treatment with sodium borohydride in ethanol. MS (ISP): 246.2 ([$\{^{37}Cl\}M+H$]$^+$), 244.2 ([$\{^{37}Cl^{35}Cl\}M+H$]$^+$), 242.1 ([$\{^{37}C\}M+H$]$^+$).

Example 26

(3,4-Difluoro-benzyl)-(1H-imidazol-2-yl)-amine

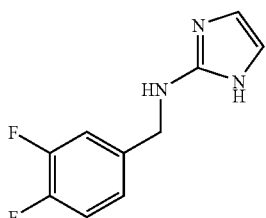

Analogously to Example 6, the title compound was obtained from 3,4-difluorobenzaldehyde, 2-aminoimidazole sulfate, tetraisopropyl orthotitanate and triethylamine in dichloromethane and treatment with sodium borohydride in ethanol. MS (ISP): 210.1 ([M+H]$^+$).

Example 27

(2,3-Difluoro-benzyl)-(1H-imidazol-2-yl)-amine

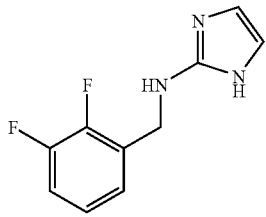

Analogously to Example 6, the title compound was obtained from 2,3-difluorobenzaldehyde, 2-aminoimidazole sulfate, tetraisopropyl orthotitanate and triethylamine in dichloromethane and treatment with sodium borohydride in ethanol. MS (ISP): 210.1 ([M+H]$^+$).

Example 28

(2-Chloro-6-ethyl-benzyl)-(1H-imidazol-2-yl)-amine

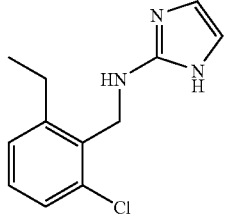

Analogously to Example 6, the title compound was obtained from 2-chloro-6-ethylbenzaldehyde, 2-aminoimidazole sulfate, tetraisopropyl orthotitanate and triethylamine in dichloromethane and treatment with sodium borohydride in ethanol. MS (ISP): 238.0 ([{$^{37}$Cl}M+H]$^+$), 236.1 ([{$^{35}$Cl}M+H]$^+$).

Example 29

(RS)-[1-(2-Chloro-phenyl)-ethyl]-(1H-imidazol-2-yl)-amine

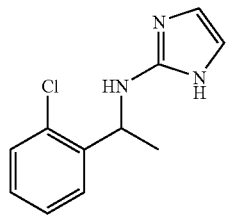

Analogously to Example 9, the title compound was obtained from 2-chloroacetophenone, 2-aminoimidazole sulfate, tetraisopropyl orthotitanate and triethylamine in dichloromethane and treatment with sodium borohydride in ethanol. MS (ISP): 224.1 ([{$^{37}$Cl}M+H]$^+$), 222.2 ([{$^{35}$Cl}M+H]$^+$).

Example 30

The ability of the compounds of the present invention to bind to TAAR1 was demonstrated in accordance with the test given hereinafter.

Materials and Methods

Construction of TAAR Expression Plasmids and Stably Transfected Cell Lines

For the construction of expression plasmids the coding sequences of human, rat and mouse TAAR1 were amplified from genomic DNA essentially as described by Lindemann et al. (2005) genomics 85, 372-385. The Expand High Fidelity PCR System (Roche Diagnostics) was used with 1.5 mM Mg$^{2+}$ and purified PCR products were cloned into pCR2.1-TOPO cloning vector (Invitrogen) following the instructions of the manufacturer. PCR products were subcloned into the pIRESneo2 vector (BD Clontech, Palo Alto, Calif.), and expression vectors were sequence verified before introduction in cell lines.

HEK293 cells (ATCC # CRL-1573) were cultured essentially as described Lindemann et al. (2005) genomics 85, 372-385. For the generation of stably transfected cell lines HEK293 cells were transfected with the pIRESneo2 expression plasmids containing the TAAR coding sequences (described above) with Lipofectamine 2000 (Invitrogen) according to the instructions of the manufacturer, and 24 hours post transfection the culture medium was supplemented with 1 mg/ml G418 (Sigma, Buchs, Switzerland). After a culture period of about 10 d clones were isolated, expanded and tested for responsiveness to trace amines (all compounds purchased from Sigma) with the cAMP Biotrak Enzyme immunoassay (EIA) System (Amersham) following the non-acetylation EIA procedure provided by the manufacturer. Monoclonal cell lines which displayed a stable EC$_{50}$ for a culture period of 15 passages were used for all subsequent studies.

Membrane Preparation and Radioligand Binding

Cells at confluence were rinsed with ice-cold phosphate buffered saline without Ca$^{2+}$ and Mg$^{2+}$ containing 10 mM EDTA and pelleted by centrifugation at 1000 rpm for 5 minutes at 4° C. The pellet was then washed twice with ice-cold phosphate buffered saline and the cell pellet was frozen immediately by immersion in liquid nitrogen and stored until use at −80° C. The cell pellet was then suspended in 20 ml HEPES-NaOH (20 mM), pH 7.4 containing 10 mM EDTA, and homogenized with a Polytron (PT 3000, Kinematica) at 10,000 rpm for 10 seconds. The homogenate was centrifuged at 48,000×g for 30 minutes at 4° C. and the pellet resuspended in 20 ml HEPES-NaOH (20 mM), pH 7.4 containing 0.1 mM EDTA (buffer A), and homogenized with a Polytron at 10,000 rpm for 10 seconds. The homogenate was then centrifuged at 48,000×g for 30 minutes at 4° C. and the pellet resuspended in 20 ml buffer A, and homogenized with a Polytron at 10,000 rpm for 10 seconds. Protein concentration was determined by the method of Pierce (Rockford, Ill.). The homogenate was then centrifuged at 48,000×g for 10 minutes at 4° C., resuspended in HEPES-NaOH (20 mM), pH 7.0 including MgCl$_2$ (10 mM) and CaCl$_2$ (2 ml) (buffer B) at 200 µg protein per ml and homogenized with a Polytron at 10,000 rpm for 10 seconds.

Binding assay was performed at 4° C. in a final volume of 1 ml, and with an incubation time of 30 minutes. The radioligand [$^3$H]-rac-2-(1,2,3,4-tetrahydro-1-naphthyl)-2-imidazoline was used at a concentration equal to the calculated K$_d$ value of 60 nM to give a total binding at around 0.1% of the total added radioligand concentration, and a specific binding which represented approximately 70-80% of the total binding. Non-specific binding was defined as the amount of [$^3$H]-rac-2-(1,2,3,4-tetrahydro-1-naphthyl)-2-imidazoline bound in the presence of the appropriate unlabelled ligand (10 µM). Competing ligands were tested in a wide range of concentrations (10 pM-30 µM). The final dimethylsulphoxide concentration in the assay was 2%, and it did not affect radioligand binding. Each experiment was performed in duplicate. All incubations were terminated by rapid filtration through UniFilter-96 plates (Packard Instrument Company) and glass filter GF/C, pre-soaked for at least 2 hours in polyethylenimine 0.3%, and using a Filtermate 96 Cell Harvester (Packard Instrument Company). The tubes and filters were then washed 3 times with 1 ml aliquots of cold buffer B. Filters were not dried and soaked in Ultima gold (45 µl/well, Packard Instrument Company) and bound radioactivity was counted by a TopCount Microplate Scintillation Counter (Packard Instrument Company).

The preferred compounds show a K$_i$ value (µM) in mouse on TAAR1 in the range of K$_i$<1.0 µM as shown in the table below.

| Compound of Example | K$_i$ (µM) mouse |
| --- | --- |
| 1 | 0.78 |
| 3 | 0.14 |
| 6 | 0.86 |
| 7 | 0.47 |
| 8 | 0.18 |
| 9 | 0.46 |
| 11 | 0.94 |
| 16 | 0.98 |
| 21 | 0.81 |
| 22 | 0.076 |
| 24 | 0.67 |
| 29 | 0.24 |

Example 31

| | Tablet Formulation (Wet Granulation) mg/tablet | | | |
|---|---|---|---|---|
| Item Ingredients | 5 mg | 25 mg | 100 mg | 500 mg |
| 1. Compound of formula I | 5 | 25 | 100 | 500 |
| 2. Lactose Anhydrous DTG | 125 | 105 | 30 | 150 |
| 3. Sta-Rx 1500 | 6 | 6 | 6 | 30 |
| 4. Microcrystalline Cellulose | 30 | 30 | 30 | 150 |
| 5. Magnesium Stearate | 1 | 1 | 1 | 1 |
| Total | 167 | 167 | 167 | 831 |

Manufacturing Procedure

1. Mix items 1, 2, 3 and 4 and granulate with purified water.

2. Dry the granules at 50° C.

3. Pass the granules through suitable milling equipment.

4. Add item 5 and mix for three minutes; compress on a suitable press.

Example 32

| | Capsule Formulation mg/capsule | | | |
|---|---|---|---|---|
| Item Ingredients | 5 mg | 25 mg | 100 mg | 500 mg |
| 1. Compound of formula I | 5 | 25 | 100 | 500 |
| 2. Hydrous Lactose | 159 | 123 | 148 | — |
| 3. Corn Starch | 25 | 35 | 40 | 70 |
| 4. Talc | 10 | 15 | 10 | 25 |
| 5. Magnesium Stearate | 1 | 2 | 2 | 5 |
| Total | 200 | 200 | 300 | 600 |

Manufacturing Procedure

1. Mix items 1, 2 and 3 in a suitable mixer for 30 minutes.

2. Add items 4 and 5 and mix for 3 minutes.

3. Fill into a suitable capsule.

The invention claimed is:

1. A compound of formula I,

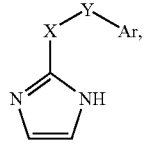

wherein
X is —NH—;
Y is —CH(lower alkyl)-; and
Ar is phenyl or naphthyl, which rings are optionally substituted by one or two substituents selected from the group consisting of halogen, lower alkoxy, lower alkyl and lower alkyl substituted by halogen;
wherein said compound is selected from the group consisting of:
(R,S)-(1H-imidazol-2-yl)-(1-phenyl-ethyl)-amine;
(R,S)-(1H-imidazol-2-yl)-(1-phenyl-propyl)-amine;
(R,S)-(1H-imidazol-2-yl)-(1-o-tolyl-ethyl)amine; and
(R,S)-[1-(2,3-dichloro-phenyl)-ethyl]-(1H-imidazol-2-yl)-amine;
or a pharmaceutically-acceptable acid-addition salts thereof.

2. A compound according to claim 1 selected from the group consisting of:
(R,S)-(1H-imidazol-2-yl)-(1-phenyl-ethyl)-amine;
(R,S)-(1H-imidazol-2-yl)-(1-o-tolyl-ethyl)amine; and
(R,S)-[1-(2,3-dichloro-phenyl)-ethyl]-(1H-imidazol-2-yl)-amine;
or a pharmaceutically-acceptable acid-addition salts thereof.

3. A compound according to claim 1 wherein said compound is (R,S)-[1-(2,3-dichloro-phenyl)-ethyl]-(1H-imidazol-2-yl)-amine or a pharmaceutically-acceptable acid-addition salt thereof.

* * * * *